United States Patent [19]

Shafer

[11] Patent Number: 5,239,106
[45] Date of Patent: Aug. 24, 1993

[54] METHOD OF RECOVERING AND PURIFYING DIPHENYLCARBONATE FROM PHENOLIC SOLUTIONS THEREOF

[75] Inventor: Sheldon J. Shafer, Pittsfield, Mass.

[73] Assignee: General Electric Company, Schenectady, N.Y.

[21] Appl. No.: 929,860

[22] Filed: Aug. 17, 1992

[51] Int. Cl.$^5$ .............................................. C07C 69/96
[52] U.S. Cl. ...................................... 558/274; 558/270
[58] Field of Search ................................ 558/274, 270

[56] References Cited

U.S. PATENT DOCUMENTS 3,251,873  5/1966  Kurkjy et al. ......................... 558/274
4,013,702  3/1977  Cartier et al. ......................... 558/270

FOREIGN PATENT DOCUMENTS 3200746  9/1991  Japan ..................................... 558/274
1096936  12/1967  United Kingdom ................. 558/274

Primary Examiner—José G. Dees
Assistant Examiner—Dwayne C. Jones
Attorney, Agent, or Firm—William A. Teoli; William H. Pittman

[57] ABSTRACT

Phenolic solutions of 20%–70% by weight of diphenylcarbonate have been found to form a crystalline 1:1 molar adduct of diphenylcarbonate and phenol when allowed to cool to a temperature between about 50° C. and 25° C. Recovery of the crystalline 1:1 molar adduct followed by distillation of phenol therefrom has been found to provide substantially pure diphenylcarbonate.

7 Claims, No Drawings

METHOD OF RECOVERING AND PURIFYING DIPHENYLCARBONATE FROM PHENOLIC SOLUTIONS THEREOF

CROSS REFERENCE TO RELATED APPLICATIONS

Reference is made to copending application with Ser. No. 07/929,861 filed Aug. 17, 1992.

BACKGROUND OF THE INVENTION

The present invention relates to a method for recovering diphenylcarbonate in substantially pure form from a solution of diphenylcarbonate and phenol. More particularly, the present invention relates to the formation of a crystalline 1:1 molar adduct of diphenylcarbonate and phenol in a solution of diphenylcarbonate and phenol, the isolation of such 1:1 molar adduct from such phenolic solution, and the recovery of diphenylcarbonate therefrom.

Prior to the present invention, diphenylcarbonate was made by a variety of procedures which resulted in the production of mixtures of diphenylcarbonate and phenol. One procedure involves the phosgenation of phenol in an aqueous environment (slurry or melt), or in a solvent such as methylene chloride. After the removal of sodium chloride, the diphenylcarbonate can be separated from residual phenol by vacuum distillation.

A second route to diphenylcarbonate is by transesterification of dimethylcarbonate with phenol. A more direct procedure for making diphenylcarbonate involves the carbonylation of phenol with carbon monoxide. A transition metal catalyst such as a palladium catalyst is used in the carbonylation route in combination with a quaternary ammonium halide. A further procedure for making diphenylcarbonate involves the reaction between a cycloalkylene carbonate and phenol.

Although various methods have been developed to make diphenylcarbonate, its recovery from a phenol containing reaction mixture in substantially pure form is often difficult to achieve. For example, the carbonylation of phenol can involve the use of a complex palladium catalyst which can include a thermally unstable quaternary ammonium halide which can generate corrosive by-products. Reaction by-products, such as phenyl salicylate and organic cocatalyst, such as benzoquinone, which can be consumed during the course of the reaction can result in additional impurities in the carbonylation reaction mixture. Although separation of unreacted phenol can be effected by distillation from the reaction mixture, the diphenylcarbonate residue can be contaminated with various catalyst ingredients.

An aqueous extraction technique based on the separation of a phenol enriched aqueous phase from a phase enriched with diphenylcarbonate also has been considered. However, it has been found difficult to form both a diphenylcarbonate phase free of water, and an aqueous phenolic phase. Satisfactory procedures for recovering diphenylcarbonate from solutions of diphenylcarbonate and phenol are therefore of significant interest to the plastics industry, since diphenylcarbonate is a valuable intermediate in the syntheses of polycarbonate resin via a transesterification process.

SUMMARY OF THE INVENTION

The present invention is based on the discovery that a single phase mixture ranging from about 20-70% by weight of diphenylcarbonate and about 80-30% by weight of phenol can form a crystalline 1:1 molar diphenylcarbonate-phenol adduct, if allowed to cool to a temperature below 51° C. The 1:1 molar crystalline adduct can be separated from the remaining liquid phase. Heating the recovered 1:1 molar crystalline adduct to a temperature of 40°-180° C. at a reduced pressure can provide the separation of phenol by distillation and a substantially pure diphenylcarbonate residue.

STATEMENT OF THE INVENTION

There is provided by the present invention, a diphenylcarbonate purification method which comprises, (1) forming a crystalline 1:1 molar adduct of diphenylcarbonate and phenol by allowing a liquid phase mixture at a temperature in the range of about 80° C. to 180° C. to cool to a temperature in the range of 50° C. to 25° C., where the liquid phase mixture comprises about 20-70% by weight of diphenylcarbonate and about 80-30% by weight of phenol, (2) recovering the crystalline 1:1 molar adduct of (1), and (3) heating the crystalline 1:1 molar adduct under reduced pressure to a temperature of up to 180° C. to effect the separation of phenol.

In the practice of a preferred form of the invention, the formation of crystalline 1:1 molar adduct of diphenylcarbonate and phenol, hereinafter referred to as "adduct", can be achieved with a solution of diphenylcarbonate and phenol, at temperatures in the range of between about 33° C. to 48° C. Such phenol and diphenylcarbonate (DPC) solutions can have an initial DPC content of about 30-60% by weight and can provide an adduct recovery of up to about 70% by weight, or up to 80% by weight of DPC.

It has been found that at a crystallizing temperature of between about 37°-41° C. with a 50% by weight solution of DPC and phenol, a 60-70% by weight recovery of adduct can be achieved. However, during recovery, the solids content of the solution can be as high as 43% by weight which often is unmanageable in large scale operations. In such situations, it has been found desirable to effect adduct crystallization in two stages, whereby each stage has a solids level of 30% by weight or less. For example, with a solution of equal parts by weight of DPC and phenol, and a crystallization temperature of about 44.5° C., 42% by weight of DPC can be recovered having an adduct solids level of about 30% by weight of solution. A second crystallization of the adduct from the remaining mother liquor at 37° C., can provide an additional 28% by weight of DPC at an adduct solids level of about 29% by weight. The total recovery of DPC from the recovered adduct utilizing standard distillation procedures at temperatures of up to 180° C., and preferably 60° to 120° C., at pressures of 10 torr to 150 torr can therefore be up to 70% by weight of DPC.

Another feature of adduct crystallization besides isolation is the ability of the adduct to reject impurities. Impurities in the initial phenol DPC mixture can vary depending upon the type of reaction used to form the DPC. For example, a solution of phenol and DPC formed during a carbonylation reaction can have such impurities as tetrabutylammonium bromide (TBAB), phenyl salicylate, and a number of side products such as, isomeric biphenols, phenolic ethers and subsequent products resulting from the carbonylation of these compounds. Although such impurities can interfere with the formation of the adduct, it has been found that upon crystallization of the adduct, such impurities which may be thermally unstable, remain behind in the mother liquor.

A convenient measuring procedure for the degree of contamination is the "rejection factor" which is defined as the mass of the contaminant in the liquid phase divided by the mass of the contaminant in the adduct phase. Accordingly, a minimum acceptable rejection factor might be 4:1, while a mixture having substantially pure adduct or a minimal amount of contamination in the adduct phase would have a substantially higher rejection factor, such as up to 100:1. Contamination of adduct crystals also can be effected with adduct liquid. The use of aqueous phenol, such as a mixture of 9% water and 91% phenol (liquified phenol) can minimize the loss of DPC by washing the adduct.

In order that those skilled in the art will be better able to practice the present invention, the following examples are given by way of illustration and not by way of limitation. All parts are by weight.

EXAMPLE 1

The following example shows the procedure for making diphenyl carbonate utilizing a gas flow reactor. The gas flow reactor is capable of delivering in a continuous manner, a mixture of carbon monoxide and oxygen maintained at a substantially constant molar ratio and partial pressure. The diphenyl carbonate was prepared by a carbonylation reaction using a palladium catalyst, tetrabutylammonium bromide, a cobalt complex containing a pentadentate Schiff base ligand, and terpyridine. The following procedure was employed:

There was added to a flow reactor, under ambient conditions, 60.29 g (641 mmol) of phenol, 4.082 g (12.7 mmol) of tetrabutylammonium bromide, 0.243 g (0.3027 mmol) of "CoSMDPT", a cobalt complex containing a pentadentate Schiff base ligand, or cobalt based di-(salicylal)-3,3'-diamino-N-methyldipropylamine, 0.0362 g (0.155 mmol) of terpyridine, and 0.0650 g (0.2895 mmol) of palladium diacetate (477 ppm palladium). In addition 26.27 g of molecular sieves (4 Angstrom) which were activated overnight at 300° C. were mounted in a perforated TEFLON resin basket above the liquid level of the reaction mixture as a dessicant. The reactor vessel was sealed. There was then fed into the reactor a mixture of 7.1% of oxygen in carbon monoxide. The mixture was introduced at the flow rate of 350 ml/min as measured with a bubbler. The pressure was set to 1650 IPSI.

The reactor was heated to 110° C. over a 15 minute period Stirring was initiated at 540–550 rpm once the reactor temperature reached 40° C. Upon reaching a reactor temperature of 110° C., aliquots were taken periodically for GC analysis in order to quantify the amount of diphenyl carbonate produced. At 0.5 hr, the yield of diphenyl carbonate was 9.79 g (14.26%). At 1.0 hr, the yield of diphenyl carbonate was 16.2 g (23.6%). At 2.0 hr, the yield of diphenyl carbonate was 23.1 g (33.7%). After the two hour sample was taken, the reaction mixture was cooled at 60° C., and depressurized to atmospheric pressure.

The above procedure was substantially repeated and the reaction mixture from the initial run at a temperature of about 50° C. was added to the second run reaction mixture at about 50° C. at atmospheric pressure.

The combined reaction mixtures were then allowed to cool to 40° C. which resulted in the separation of a DPC/phenol adduct. The DPC/phenol adduct was recovered from the reaction mixture by vacuum filtration resulting in the recovery of 58.5 g of the adduct representing a 74% yield. The DPC/phenol adduct was then heated to a temperature of 120° C. at a pressure of 80 torr to effect the distillation of phenol which resulted in the recovery of about 33.4 g of diphenyl carbonate.

EXAMPLE 2

A molten mixture maintained at 80° C. of 50 grams of phenol and 50 grams of diphenylcarbonate was cooled to 41° C. Upon cooling, crystals began to form, after 1 hour at 41° C.; the crystals were separated from the liquid phase by filtration. The crystals weighed 43.2 grams and have a melting point of 51° C. HPLC analysis of the crystals indicated a composition having 69.5% diphenylcarbonate and 30.5% phenol (a 1:1 molar adduct). The adduct was heated at 120° C. under 80 torr to effect distilation of phenol from the crystalline product. Overall recovery of diphenylcarbonate from the initial mixture was 60%.

EXAMPLE 3

A molten mixture of 60 grams of phenol and 40 grams of diphenylcarbonate maintained at 100° C. was cooled to 35° C. After 1 hour at 35° C., the crystals which formed were removed by filtration. The crystals were found to have the same melting point (51° C.) and composition (69.5% diphenylcarbonate, 30.5% phenol) as the crystals in Example 2. Overall recovery of diphenylcarbonate from the initial mixture was 53%, following the separation of phenol by distillation in accordance with the procedure of Example 2.

EXAMPLE 4

A 100 gram sample of a mixture which was 54.1% by weight diphenylcarbonate, 44.6% phenol and 1.3% phenyl salicylate was cooled from 100° C. to 44° C. Upon cooling, crystals formed and after 1 hour at 44° C. the crystals were separated from the liquid phase by filtration. The crystals weighed 45.9 grams. HPLC analysis of the crystals indicated that the composition was 69.3% by weight diphenylcarbonate, 30.7% phenol, with a trace of phenyl salicylate (30 ppm). HPLC analysis of the liquid phase indicated the following weight % composition: 41.2% diphenylcarbonate, 56.4% phenol and 2.4% phenyl salicylate. The overall recovery of diphenylcarbonate via the adduct from the initial composition was 58.8%, following the procedure of Example 2.

EXAMPLE 5

A mixture of 50 grams of phenol and 50 grams of diphenylcarbonate at 80° C. was cooled to 45° C., then maintained at 45° C. for 1 hour. A mixture having about 30% solids was produced. A diphenylcarbonate/phenol adduct was recovered by filtration. There was obtained, 30.2 grams of adduct which provided 21 grams of diphenylcarbonate upon phenol distillation.

After adduct recovery, the mother liquor was cooled to 37° C., then held at 37° C. for 1 hour. A mixture having about 30% solids was produced. Additional diphenylcarbonate/phenol adduct was removed by filtration. There was obtained 20.4 grams of adduct which yields 14.29 grams of DPC. The overall recovery of diphenylcarbonate by this two stage procedure was 70% by weight.

What is claimed is:

1. A diphenylcarbonate purification method which comprises,
   (1) forming a crystalline 1:1 molar adduct of diphenylcarbonate and phenol by allowing a liquid phase mixture at a temperature in the range of about 80° C. to 180° C. to cool to a temperature in the range of 50° C. to 25° C., where the liquid phase mixture comprises about 20-70% by weight of diphenylcarbonate and about 80-30% by weight of phenol,
   (2) recovering the crystalline 1:1 molar adduct of (1), and
   (3) heating the crystalline 1:1 molar adduct under reduced pressure to a temperature of up to 180° C. to effect the separation of phenol.

2. A method in accordance with claim 1, where the liquid phase mixture is made by the carbonylation of phenol.

3. A method in accordance with claim 1, where the liquid phase mixture is made by the phosgenation of phenol.

4. A method in accordance with claim 1, where the liquid phase mixture is made by the transesterification of dimethylcarbonate and phenol.

5. A method in accordance with claim 1, where the liquid phase mixture is made by the reaction of a cycloalkylenecarbonate and a phenol.

6. A method in accordance with claim 1, where at least 2 stages of adduct crystallization are employed to reduce the solids level in the crystallization mixture prior to the recovery of the crystalline 1:1 molar adduct from the mixture.

7. A method in accordance with claim 1, where the crystalline 1:1 molar adduct is treated with a wash solvent prior to being heated under reduced pressure to effect the separation of phenol.

* * * * *